US009931249B2

(12) United States Patent
Sealy et al.

(10) Patent No.: US 9,931,249 B2
(45) Date of Patent: *Apr. 3, 2018

(54) REDUCED-PRESSURE, DEEP-TISSUE CLOSURE SYSTEMS AND METHODS

(71) Applicant: KCI Licensing, Inc., San Antonio, TX (US)

(72) Inventors: James Joseph Sealy, Hants (GB); Keith Patrick Heaton, Poole (GB); Colin John Hall, Poole (GB); Christopher Guy Coward, Wareham (GB); Mark Stephen James Beard, Ferndown (GB)

(73) Assignee: KCI Licensing, Inc., San Antonio, TX (US)

(*) Notice: Subject to any disclaimer, the term of this patent is extended or adjusted under 35 U.S.C. 154(b) by 378 days.

This patent is subject to a terminal disclaimer.

(21) Appl. No.: 14/528,786

(22) Filed: Oct. 30, 2014

(65) Prior Publication Data
US 2015/0065968 A1 Mar. 5, 2015

Related U.S. Application Data

(62) Division of application No. 12/467,123, filed on May 15, 2009, now Pat. No. 8,936,618.
(Continued)

(51) Int. Cl.
A61F 13/00 (2006.01)
A61B 17/00 (2006.01)
A61M 1/00 (2006.01)

(52) U.S. Cl.
CPC .... A61F 13/00068 (2013.01); A61B 17/0057 (2013.01); A61F 13/00025 (2013.01);
(Continued)

(58) Field of Classification Search
CPC .......... A61F 13/00068; A61F 13/00004; A61F 13/00987; A61F 13/00034;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

EP15180495; EP Search Report; dated Dec. 15, 2015; 3 pages.
(Continued)

Primary Examiner — Jocelin Tanner

(57) ABSTRACT

A reduced-pressure, deep-tissue closure device for applying a closing force on a deep tissue includes a contractible matrix that is formed with a first plurality of apertures and which has a first side and a second, inward-facing side. The contractible matrix is for disposing proximate to the deep tissue. A reduced-pressure source is fluidly coupled to the contractible matrix and operable to deliver reduced pressure to the contractible matrix. When under reduced pressure, the contractible matrix grips the deep tissue adjacent the contractible matrix and provides a closing force on the deep tissue. A system and method are also presented.

11 Claims, 3 Drawing Sheets

Related U.S. Application Data

(60) Provisional application No. 61/109,448, filed on Oct. 29, 2008, provisional application No. 61/109,486, filed on Oct. 29, 2008, provisional application No. 61/109,390, filed on Oct. 29, 2008, provisional application No. 61/109,410, filed on Oct. 29, 2008.

(52) U.S. Cl.
CPC .. *A61F 13/00034* (2013.01); *A61F 13/00987* (2013.01); *A61M 1/0088* (2013.01); *A61B 2017/00575* (2013.01); *A61B 2017/00646* (2013.01); *A61B 2017/00676* (2013.01); *A61F 13/00029* (2013.01); *A61F 13/00038* (2013.01); *A61M 1/0092* (2014.02); *Y10T 29/49* (2015.01); *Y10T 29/49826* (2015.01); *Y10T 156/1052* (2015.01); *Y10T 156/1056* (2015.01); *Y10T 156/1057* (2015.01); *Y10T 156/1062* (2015.01); *Y10T 156/1304* (2015.01)

(58) Field of Classification Search
CPC .......... A61F 13/00025; A61F 13/00038; A61F 13/00029; A61F 2013/00089; A61B 17/0057; A61B 2017/00646; A61B 2017/00575; A61B 2017/00676; A61M 1/0092; Y10T 156/1056; Y10T 156/1062; Y10T 156/1057; Y10T 156/1304; Y10T 156/1052; Y10T 29/49; Y10T 29/49826
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,815,601 A * | 6/1974 | Schaefer | A61F 13/2051 604/15 |
| 3,826,254 A | 7/1974 | Mellor | |
| 3,970,324 A * | 7/1976 | Howat | A63C 5/12 156/197 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,936,615 B2 * | 1/2015 | Pappalardo | A61B 17/8019 606/105 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0030304 A1 * | 2/2004 | Hunt | A61M 1/0088 604/317 |
| 2006/0079852 A1 | 4/2006 | Bubb et al. | |
| 2006/0189910 A1 | 8/2006 | Johnson et al. | |
| 2008/0125687 A1 * | 5/2008 | Flick | A61F 13/00063 602/48 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |

(56) References Cited

FOREIGN PATENT DOCUMENTS

| | | |
|---|---|---|
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2342584 A | 4/2000 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 01/85248 A1 | 11/2001 |
| WO | 2007031762 A1 | 3/2007 |
| WO | 2007041642 A2 | 4/2007 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation

(56) References Cited

OTHER PUBLICATIONS

Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

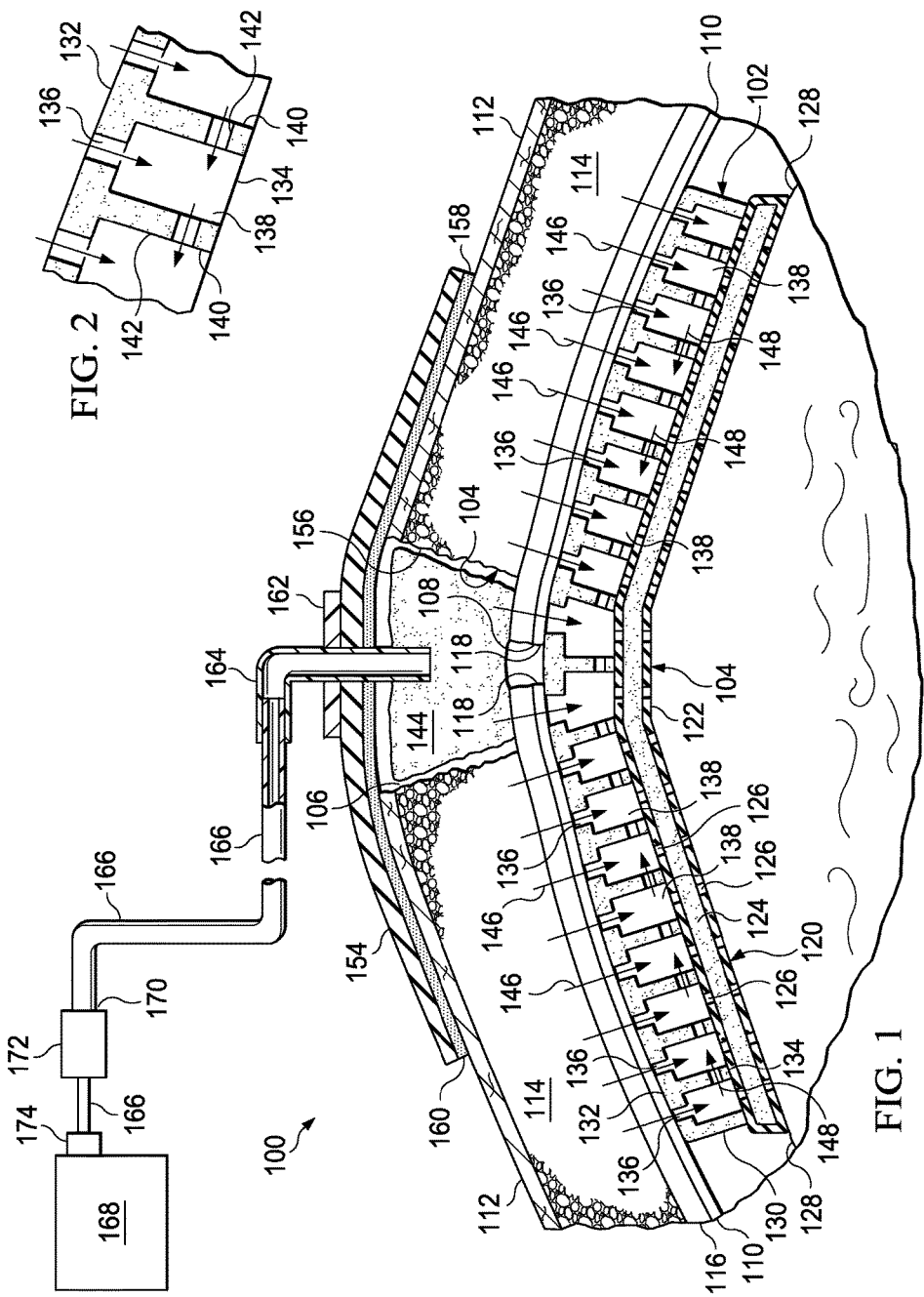

REDUCED-PRESSURE, DEEP-TISSUE CLOSURE SYSTEMS AND METHODS

RELATED APPLICATIONS

This application is a Divisional of U.S. patent application Ser. No. 12/467,123, filed May 15, 2009 which claims the benefit, under 35 USC § 119(e), of the filing of: U.S. Provisional Patent Application Ser. No. 61/109,448, entitled "Reduced-Pressure, Deep-Tissue Closure System and Method," filed Oct. 29, 2008; U.S. Provisional Patent Application Ser. No. 61/109,486, entitled "Reduced-Pressure, Abdominal Treatment System and Method," filed Oct. 29, 2008; U.S. Provisional Patent Application Ser. No. 61/109,390, entitled "Open-Cavity, Reduced-Pressure Wound Dressing and System," filed Oct. 29, 2008; and U.S. Provisional Patent Application Ser. No. 61/109,410, entitled "Reduced-Pressure, Wound-Closure System and Method," filed Oct. 29, 2008. All of these provisional applications are incorporated herein by reference for all purposes.

BACKGROUND

The present invention relates generally to medical treatment systems and, more particularly, to reduced-pressure, deep-tissue closure systems and methods.

Whether the etiology of a wound, or damaged area of tissue, is trauma, surgery, or another cause, proper care of the wound, or wounds, is important to the outcome. Unique challenges exist when the wound involves locations that require reentry, for example, the peritoneal cavity and more generally the abdominal cavity. Often times when surgery or trauma involves the abdominal cavity, establishing a wound management system that facilitates reentry allows for better and easier care and helps to address such things as peritonitis, abdominal compartment syndrome, and infections that might inhibit final healing of the wound and the internal organs. In providing such care, it may be desirable to remove unwanted fluids from the cavity, help approximate to the fascia and other tissues, and finally to help provide a closing force on the wound itself at the level of the epidermis.

A number of deep tissues, e.g., fat, muscle, or particularly fascia, may need to be addressed when one is temporarily closing the abdomen. Unless otherwise indicated, as used herein, "or" does not require mutual exclusivity. If not addressed, the deep tissue may retract further into the abdominal cavity and subsequently cause difficulties. The surgeon may suture the deep tissue, e.g., the fascia, while placing the fascia under tension. This can be problematic, however, if reduced-pressure treatment in the area is desired or if the dressing needs to be replaced. Moreover, suturing the deep tissue can at times cause necrosis. If a complex wound, e.g., a wound that is infected, is involved, the fascia may be very fragile and may not be able to endure suturing. If a mesh is used to assist in the latter situation, removal of the mesh can be difficult and may require surgery. At the same time, if the deep tissue, notably the fascia, is not closed, the situation can lead to hernias and other complications.

In addition to accessing the cavity for reentry, it may be desirable to remove fluids from the cavity. It may also be desirable to provide reduced-pressure therapy to the tissue or wound, including wounds that may be within the abdominal cavity. This treatment (frequently referred to in the medical community as "negative pressure wound therapy," "reduced pressure therapy," or "vacuum therapy") may provide a number of benefits, including faster healing and increased formulation of granulation tissue.

It would be desirable to provide a system and method that could facilitate reduced-pressure treatment and help close the deep tissue in a way that avoids or minimizes complications, such as the retraction of deep tissue or necrosis.

SUMMARY

Problems with existing deep tissue closing systems, devices, and methods are addressed by the systems, devices, and methods of the illustrative embodiments described herein. According to one illustrative embodiment, a reduced-pressure, deep-tissue closure system for applying a closing force proximate to a deep tissue includes a contractible matrix being formed with a first plurality of apertures, and having a first side and a second, inward-facing side. A reduced-pressure source is fluidly coupled to the contractible matrix and operable to deliver reduced pressure to the contractible matrix.

According to another illustrative embodiment, a reduced-pressure, deep-tissue closure system for applying a closing force proximate to a deep tissue includes a contractible matrix being formed with a first plurality of apertures and having a first side and a second, inward-facing side. The second side is formed with a first plurality of cells, each open cell having cell walls. A second plurality of apertures is formed in the cell walls. A reduced-pressure source is fluidly coupled to the contractible matrix and operable to deliver reduced pressure to the contractible matrix.

According to another illustrative embodiment, a reduced-pressure treatment system for applying a closing force to a deep-tissue wound in a body cavity of a patient includes a contractible matrix being formed with a first plurality of apertures and having a first side and a second, inward-facing side. The second side is formed with a plurality of cells and with a second plurality of apertures. The illustrative reduced-pressure treatment system also includes a manifold member operable to distribute a reduced pressure and a reduced-pressure source fluidly coupled to the manifold member and to the contractible matrix. The reduced-pressure source delivers reduced pressure to the manifold member and to the contractible matrix. The illustrative reduced-pressure treatment system also includes a sealing member operable to provide a pneumatic seal over the body cavity.

According to another illustrative embodiment, a method of manufacturing a reduced-pressure treatment system for applying a closing force to a deep tissue in a body cavity of a patient includes the steps of: forming a contractible matrix having a first plurality of apertures, and having a first side and a second, inward-facing side. The second side is formed with a plurality of cells and further being formed with a second plurality of apertures. The method further includes providing a manifold member operable to distribute a reduced pressure and providing a sealing member operable to provide a pneumatic seal over the body cavity.

According to another illustrative embodiment, a method of providing a closing force to a deep tissue in a body cavity of a patient includes the step of placing a contractible matrix in the body cavity adjacent the deep tissue. The contractible matrix is formed with a plurality of apertures and has a first side and a second, inward-facing side. The second side being formed with a first plurality of cells and with a second plurality of apertures. The method may further include fluidly coupling a reduced-pressure source to the contractible matrix and sealing the body cavity with a sealing member.

Other objects, features, and advantages of the illustrative embodiments will become apparent with reference to the drawings and detailed description that follow.

BRIEF DESCRIPTION OF THE DRAWINGS

FIG. 1 is a schematic diagram, with a portion in cross section, of an illustrative embodiment of a reduced-pressure, deep-tissue closure system;

FIG. 2 is a schematic, cross-sectional view of a detail of the illustrative reduced-pressure, deep-tissue closure system of FIG. 1 showing a portion of a contractible matrix;

DETAILED DESCRIPTION OF ILLUSTRATIVE EMBODIMENTS

Figure 3:
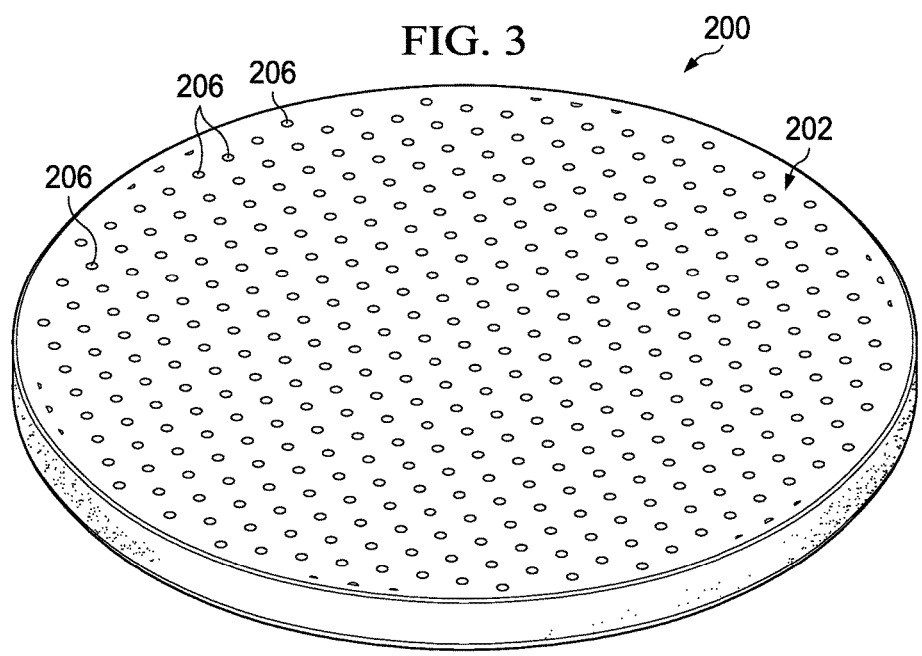
FIG. 3 is a schematic, perspective view of a first side of an illustrative contractible matrix.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Referring to FIGS. 1-2, a reduced-pressure, deep-tissue closure system 100, which includes a reduced-pressure, deep-tissue closure device 102, is presented. The reduced-pressure, deep-tissue closure system 100 and the reduced-pressure, deep-tissue closure device 102 are for use proximate to a tissue site 104 within a body cavity 106 that involves a deep-tissue, such as a deep-tissue wound 108 in the patient's fascia 110. In some instances, the closure system 100 and closure device 102 may be used on other tissues. As used herein, "wound" refers to a damaged area of tissue or tissues irrespective of the cause of the damage.

In this illustrative embodiment, a wound extends through a patient's epidermis 112, fat layer 114, muscle 116, and fascia 110. Of these layers, particular attention is often given to closing the fascia 110. While this illustrative embodiment focuses on fascia 110, it should be understood that the reduced-pressure, deep-tissue closure system 100 and the reduced-pressure, deep-tissue closure device 102 could be used on other deep-tissues or deep-tissue wounds.

The deep-tissue wound 108 in the fascia 110, in this illustration, involves a laceration or incision creating fascia edges 118. It is desired to close or urge the fascia edges 118 together with a closing force. As used herein, unless otherwise indicated, "or" does not require mutual exclusivity. When reentry may be needed, a temporary closure of the fascia 110 is preferred. Thus, it is desirable to close or apply a closing force on the fascia 110 by proximating the fascia edges 118. As will be described more below, the reduced-pressure, deep-tissue closure device 102 of this illustrative embodiment helps to close or apply a closing force on the fascia 110.

In this illustrative embodiment, the body cavity 106 is an abdominal cavity and the tissue site 104 is a portion of an abdominal contents 122 or the tissue proximate to the abdominal contents 122. In providing open wound management utilizing the reduced-pressure, deep-tissue closure system 100, it may be desirable to first place a body-cavity dressing 120 on the abdominal contents 122. The abdominal contents 122 provide support for the body-cavity dressing 120.

The body-cavity dressing 120 may include a non-adherent, encapsulated manifold member 124. The encapsulating layers of the body-cavity dressing 120 may be formed with fenestrations or apertures, such as apertures 126, that allow fluids to enter the body-cavity dressing 120. The body-cavity dressing 120 may be formed with a non-adherent drape that has a discrete plurality of leg members. The body-cavity dressing 120 is positioned on the abdominal contents 122 and preferably positioned, at least in part, into one or more of the paracolic gutters 128. The reduced-pressure, deep-tissue closure device 102 may then be disposed the adjacent body-cavity dressing 120 just underneath (for the orientation shown in FIG. 1) the fascia 110.

The reduced-pressure, deep-tissue closure device 102 includes a contractible matrix 130, which has a first side 132 and a second, inward-facing (patient-facing) side 134. The first side 132 is for placing adjacent to the tissue layer, e.g., the fascia 110, which the closure device 102 is intended to close or urge together. The contractible matrix 130 may be formed with a first plurality of apertures 136 through a contractible material or structure. The first plurality of apertures 136 may take any shape, e.g., slits (linear openings), rectangular openings, irregular-shaped openings, etc. The contractible matrix 130 may be formed with a plurality of cells, or compartments or partial compartments, e.g., open cells 138, on the second, inward-facing side 134 or on any portion of the contractible matrix 130. The first plurality of apertures 136 may be in fluid communication with the first plurality of cells 138. As shown in FIG. 2, the first plurality of cells 138 may be formed with cell walls 140 and may include a second plurality of apertures 142.

When reduced pressure is delivered to the contractible matrix 130, a gripping force is developed and an inward force. The reduced pressure acts through the first plurality of apertures 136 to provide the gripping force on the fascia 110. The gripping force holds, or grips, the fascia 110. The reduced pressure may be supplied to the contractible matrix 130 from underneath (for the orientation shown) through the body-cavity dressing 120 and in particular through apertures 126 or through a manifold 144. The gripping force on the fascia 110 is represented by arrows 146.

In addition to providing a gripping force through the apertures 136, the reduced pressure also urges the contractible matrix 130 inward, i.e., in the direction shown by arrows 148. "Inward" in this context means toward a center portion of the reduced-pressure, deep-tissue closure device 102. Alternatively, "inward" may be defined as in a direction that would pull the tissue, e.g., the fascia 110, towards the edges 118 of the tissue wound 108 for a deployed reduced-pressure, deep-tissue closure device 102. As the reduced pressure acts on the contractible matrix 130, the contractible matrix 130 grips the fascia 110 and changes from a non-contracted position to a contracted position. In one embodiment, the contractible matrix 130 includes cells that collapse laterally and thereby contract. The side walls, which are flexible, of the cells move closer to one another under the influence of reduced pressure. Because the reduced pressure on the first plurality of apertures 136 grips the fascia 110, and the reduced pressure also causes the contractible matrix 130 to contract, a closing force is developed and applied to the fascia 110 that urges the fascia edges 118 into closer approximation. Thus, the fascia 110 experiences a closing force and that causes the fascia 110 to be closed or urged into a closed position.

In one embodiment, the contractible matrix 130 includes a plurality of cells, e.g., cells 138, that collectively define a first volume ($V_1$) when no reduced pressure is applied. When reduced pressure is applied to the cells, the cells collapse or otherwise move such that a second volume is defined ($V_2$). The second volume is less than the first volume ($V_1$), i.e., $V_1 > V_2$, and this change in volume is associated with contraction.

As used herein, "reduced pressure" generally refers to a pressure less than the ambient pressure at the tissue site 104 that is being subjected to treatment. In most cases, this reduced pressure will be less than the atmospheric pressure at which the patient is located. Alternatively, the reduced pressure may be less than a hydrostatic pressure at the tissue site 104. Unless otherwise indicated, values of pressure stated herein are gauge pressures.

The manifold 144 is placed within the body cavity 106 proximate to the reduced-pressure, deep-tissue closure device 102, which is proximate to the body-cavity dressing 120. The manifold 144 may be supported by or be disposed adjacent the first side 132 of the contractible matrix 130. The term "manifold" as used herein generally refers to a substance or structure that is provided to assist in applying reduced pressure to, delivering fluids to, or removing fluids from the tissue site 104 or other location. The manifold 144 typically includes a plurality of flow channels or pathways that distribute fluids provided to and removed from the area around the manifold 144. The manifold 144 may include a plurality of flow channels or pathways that are interconnected to improve distribution of fluids. The manifold 144 may be a biocompatible material that is capable of being placed in contact with tissue. Examples of manifold 144 may include, without limitation, devices that have structural elements arranged to form flow channels, cellular foam, such as open-cell foam, porous tissue collections, and liquids, gels, and foams that include or cure to include flow channels. The manifold 144 may be porous and may be made from foam, gauze, felted mat, or any other material suited to a particular biological application. In one embodiment, the manifold 144 is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. Other embodiments might include "closed cells." These closed-cell portions of the manifold 144 contain a plurality of cells, the majority of which are not fluidly connected to adjacent cells. The closed cells may be selectively disposed in the manifold 144 to prevent transmission of fluids through perimeter surfaces of the manifold 144. In some situations, the manifold 144 may also be used to distribute fluids, such as medications, antibacterials, growth factors, and other solutions to the wound 108 or the body cavity 106. Other layers or material might be included as part of the manifold 144, such as absorptive material, wicking material, hydrophobic material, hydrophilic material, etc.

A sealing member 154 is placed over a body-cavity opening 156 of the body cavity 106 and provides a pneumatic seal adequate for the reduced-pressure, deep-tissue closure system 100 to hold reduced pressure within the body cavity 106. The sealing member 154 may be a cover that is also used to secure the manifold 144 on a central portion of the body-cavity dressing 120. While the sealing member 154 may be impermeable or semi-permeable, the sealing member 154 is capable of maintaining a reduced pressure at the tissue site 104 after installation of the sealing member 154 over the body-cavity opening 156. The sealing member 154 may be a flexible over-drape or film formed from a silicone based compound, acrylic, hydrogel or hydrogel-forming material, or any other biocompatible material that includes the impermeability or permeability characteristics desired for use with a tissue site or the reduced-pressure, deep-tissue closure device 102.

The sealing member 154 may further include an attachment means 158 to secure the sealing member 154 to the patient's epidermis 112. The attachment means 158 may take many forms. For example, the attachment means 158 may include an adhesive 160 positioned on the sealing member 154 or on any portion of the sealing member 154 to provide the pneumatic seal. The adhesive 160 might be pre-applied and covered with a releasable backing, or member, that is removed at the time of application to the patient.

A reduced-pressure interface 162, such as an elbow port 164, may be applied to the sealing member 154 to provide reduced pressure through the sealing member 154 and to the manifold 144 and thereby to the contractible matrix 130. The reduced-pressure interface 162 may be used for this purpose, but other approaches may also be used. For example, in one embodiment (not shown), a reduced-pressure delivery conduit 166 is placed directly into the manifold 144. In the illustrative embodiment shown, the reduced-pressure delivery conduit 166 is fluidly coupled to a reduced-pressure source 168.

The reduced-pressure source 168 may accommodate a wide range of reduced pressures. The range may include −50 to −400 mm Hg. In one illustrative embodiment, the reduced-pressure source 168 may include preset selectors for −100 mm Hg, −125 mm Hg, and −150 mm Hg. The reduced-pressure source 168 may also include a number of alarms, such as a blockage alarm, a leakage alarm, or a battery-low alarm. The reduced-pressure source 168 could be a portable source, wall source, or other unit for abdominal cavities. The reduced-pressure source 168 may selectively deliver a constant pressure, intermittent pressure, dynamic pressure, or pressure with a set pattern.

A medial portion 170 of the reduced-pressure delivery conduit 166 may include a number of devices, such as a representative device 172. The device 172 might be a fluid collection member, or canister reservoir, to hold exudates, ascites, and other fluids removed; a pressure feedback device; a volume detection system; a blood detection system; an infection detection system; a flow monitoring system; a filter; a temperature monitoring system; etc. Some representative devices 172, e.g., the fluid collection member, may be formed integral to the reduced-pressure source 168. For example, a reduced-pressure port 174 on the reduced-pressure source 168 may include a filter member that includes one or more filters, such as a hydrophobic filter that prevents liquid from entering an interior space. Multiple devices might be included.

The reduced-pressure, deep-tissue closure system 100 is operable to provide a closing force on the fascia 110. In addition, the reduced-pressure, deep-tissue closure system may provide reduced-pressure treatment within the body cavity 106 and at or proximate to the tissue site 104. The reduced-pressure treatment may be applied within the body cavity 106 and at the tissue site 104 to help promote removal of ascites, exudates, or other fluids. The reduced pressure may also stimulate the growth of additional tissue. In the case of a wound at the tissue site 104, the growth of granulation tissue and removal of exudates and bacteria may help to promote healing. In the situation of a non-wounded or non-defective tissue at the tissue site 104, reduced pressure may be used to promote the growth of tissue that may be harvested and transplanted to another tissue site.

In operation, after the body-cavity dressing 120 has been disposed within the body cavity 106 and adjacent the abdominal contents 122, the reduced-pressure, deep-tissue closure device 102 may be disposed adjacent the reduced-pressure, deep-tissue closure device 102 and underneath (for the orientation shown in FIG. 1) the fascia 110. The manifold 144 may then be inserted into the body cavity 106 and disposed proximate to the reduced-pressure, deep-tissue closure device 102. The sealing member 154 may then be disposed on the patient's epidermis 112 over the body-cavity opening 156 to form a pneumatic seal over the body cavity 106. The reduced-pressure interface 162, e.g., elbow port 164, may be attached to the sealing member 154. The reduced-pressure delivery conduit 166 may be fluidly coupled between the reduced-pressure interface 162 and the reduced-pressure source 168.

When the reduced-pressure source 168 is activated, the reduced pressure is delivered through the reduced-pressure delivery conduit 166 to the reduced-pressure interface 162 and thereby to the manifold 144 and to the reduced-pressure, deep-tissue closure device 102. The reduced pressure experienced by the reduced-pressure, deep-tissue closure device 102 causes the reduced-pressure, deep-tissue closure device 102 to grip the fascia 110 through the first plurality of apertures 136 and to contract. As the reduced-pressure, deep-tissue closure device 102 contracts, a closing force is experienced by the fascia 110 that is directed towards the fascia edges 118. The fascia edges 118 are thereby approximated. The closing force experienced by fascia 110 is developed without the need to puncture or wound the fascia 110 or other tissue. In addition to approximating the fascia edges 118, the reduced pressure supplied to the reduced-pressure interface 162, and thereby to the manifold 144, provides for reduced-pressure treatment in the body cavity 106 and may provide reduced-pressure treatment to tissue proximate to the tissue site 104.

Figure 4:
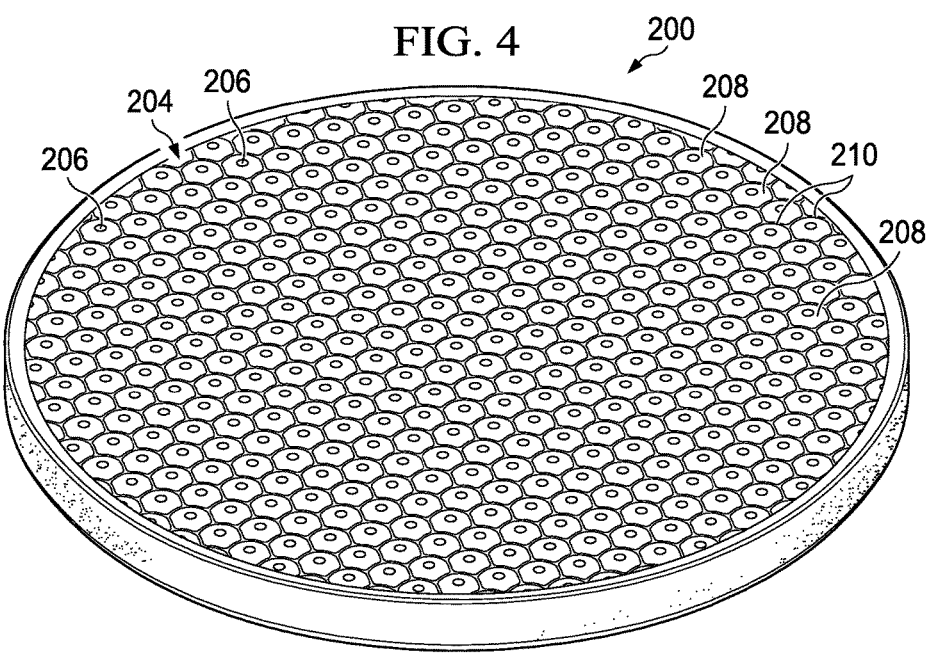
FIG. 4 is a schematic, perspective view of a second side of the illustrative contractible matrix of FIG. 3.

Referring now to FIGS. 3 and 4, another illustrative contractible matrix 200 is presented. The contractible matrix 200 has a first side 202 and a second, inward-facing side 204. FIG. 3 presents the first side 202, and FIG. 4 presents the second, inward-facing side 204. The contractible matrix 200 may be used in the reduced-pressure, deep-tissue closure system 100 of FIG. 1. In this particular illustrative embodiment, the contractible matrix 200 is formed with a solid circular shape, but numerous other shapes, such as the elliptical shape shown in FIG. 5, an arcuate shape, rectangular shape, etc., may be used. The first side 202 of the contractible matrix 200 has a first plurality of apertures 206 formed there through and that extend to the second, inward-facing side 204. As shown in FIG. 4, a plurality of cells 208 is formed on the second, inward-facing side 204. Each cell of the plurality of cells 208 has cell walls 210. The cells 208 each have an aperture 206 and an open cell portion. Each cell wall 210 may have one or more apertures through the cell wall 210 to form a second plurality of apertures analogous to the second plurality of apertures 142 in FIG. 2. In this particular illustrative embodiment, the plurality of cells 208 may be formed as honeycomb cells centered around each of the first plurality of apertures 206.

Figure 5:
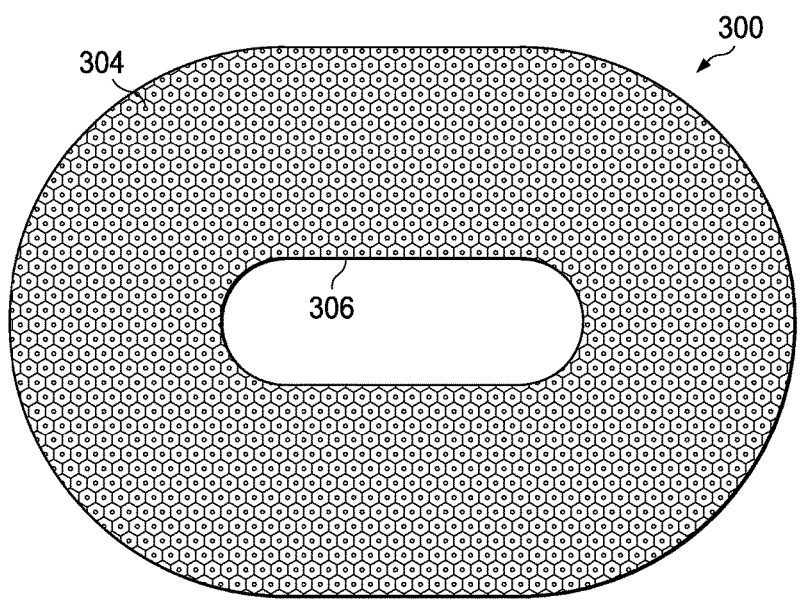
FIG. 5 is a schematic, top view of another illustrative embodiment of a contractible matrix.
Figure 6:
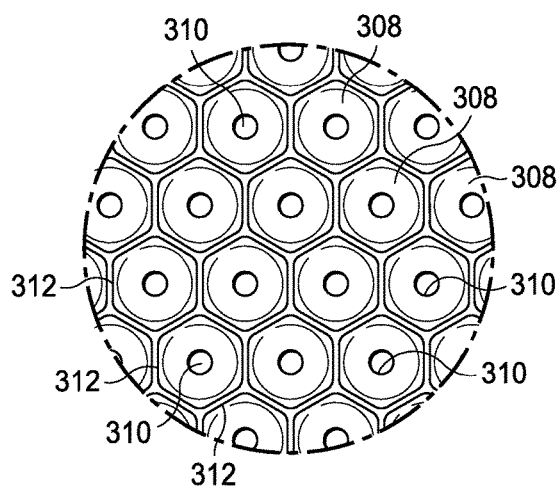
FIG. 6 is a detail of a portion of the contractible matrix of FIG. 5.

Referring now to FIGS. 5 and 6, another illustrative embodiment of a contractible matrix 300 is presented. The contractible matrix 300 may be used in the reduced-pressure, deep-tissue closure system 100 of FIG. 1. The contractible matrix 300 has a first side (not shown) and a second, inward-facing side 304. The contractible matrix 300 in this particular illustrative embodiment is formed with an oval shape that has a central opening 306, but the contractible matrix 300 could be formed without the central opening 306. The second, inward-facing side 304 of the contractible matrix 300 may be formed with a plurality of cells 308. A first plurality of apertures 310 may be formed through the contractible matrix 300 and may be in fluid communication with the plurality of cells 308. The plurality of cells 308 may be formed by a plurality of interconnected cell walls 312. As with the embodiment shown in FIG. 2, the plurality of interconnected cell walls 312 may be formed with intercellular apertures (not shown) to form a second plurality of apertures.

Figure 7:
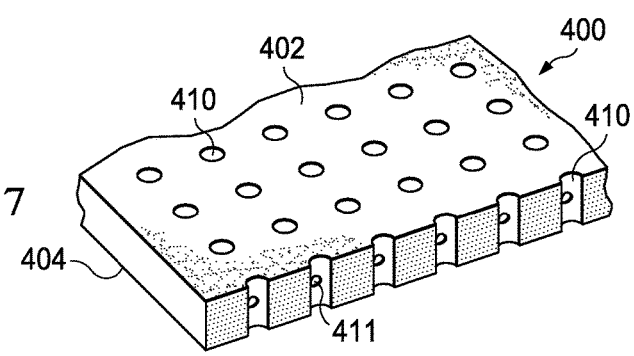
FIG. 7 is a schematic, perspective view of another illustrative embodiment of a contractible matrix.

Referring now to FIG. 7 another illustrative embodiment of a contractible matrix 400 is presented. The contractible matrix 400 may be used in the reduced-pressure, deep-tissue closure system 100 of FIG. 1. The contractible matrix 400 in this illustrative embodiment is rectangular in shape and has a first plurality of apertures 410 that go from a first side 402 to a second, inward-facing side 404 of the contractible matrix 400. A second plurality of apertures 411 may connect the first plurality of apertures 410 or some portion thereof.

In an alternative embodiment, the contractible matrix 400 may have apertures 410 on the first side 402 but no corresponding aperture on the second, inward-facing side 404. Thus, the contractible matrix 400 has cells that open only to the first side 402 and may have apertures 411, which provide reduced pressure into the cells. When reduced pressure is supplied through apertures 411, the deep tissue is gripped by the apertures 410 and the side walls of the cells are pulled into closer proximity causing the contractible matrix 400 to contract.

A number of different substances might be used to form the contractible matrix 130 (FIG. 1), contractible matrix 200 (FIGS. 3 and 4), contractible matrix 300 (FIGS. 5 and 6), and contractible matrix 400 (FIG. 7). Typically, a flexible, contractible material is used. For example, these contractible matrices 130, 200, 300, 400 may be formed from flexible, thermal plastic elastomers (TPE); thermoplastic urethane (TPU); silicone rubber; etc. Moreover, a number of different cell geometries may be utilized in the contractible matrices. For example, the possible cell geometries include honeycomb, round-shaped, diamond-shaped, gear-shaped cells, etc. Foam is not used for the contractible matrices. The material from which the contractible matrices are formed preferably avoid the in growth of any tissue. In one illustrative embodiment, the contractible matrix may be formed with a TPU honeycomb material that includes honeycomb cells that are formed with fusion bonding. While foam is not used typically, in one embodiment, the contractible matrix could be formed from a sealed or encapsulated foam member that has apertures for gripping the tissue and a reduced-pressure supply interface.

In another illustrative embodiment, the contractible matrix may be formed from a thermal plastic elastomer (TPE) that allows for expansion and contraction in the xy plane (the plane within the page for FIG. 5) while holding a fairly constant dimension in the z direction (coming out of the page on FIG. 5). In this embodiment, the contractible matrix may have a stronger material (or more material) concentrated in the z direction than in the xy directions. Alternatively or in addition, voids may be add to prescribe the pattern of collapse. Alternatively or in addition, strengthening members, e.g., filaments, may be added in the z direction to avoid collapse in that direction. In another illustrative embodiment, the contractible matrix may be formed using a thermoplastic urethane (TPU) material that may have an additional film on the contractible matrix on the first side, e.g., on side 302 of the contractible matrix 300 of FIG. 5. These are only some illustrative examples.

In an alternative embodiment, a contract matrix may be formed to contract under reduced pressure by utilizing a pneumatic element, or device, that contracts under reduced pressure. Thus, for example, with reference to FIG. 7, the apertures 410 may be sealed on the top and bottom to form a plurality of pneumatic chambers. The second apertures 411 may remain open to receive reduced pressure. As reduced pressure is delivered to the chambers formed from the first apertures 410, the chambers collapse and provide a contracting force inward. Other pneumatic devices may utilized, but in each instance the pneumatic device preferably grips the fascia without causing a wound and contracts under reduced pressure.

Although the present invention and its advantages have been disclosed in the context of certain illustrative, non-limiting embodiments, it should be understood that various changes, substitutions, and alterations can be made without departing from the scope of the invention as defined by the appended claims.

We claim:

1. A reduced-pressure, tissue closure system for applying a closing force proximate to a tissue, the reduced-pressure, tissue closure system comprising:
   a contractible matrix comprising a first side, a first plurality of apertures in the first side, a second side, and a plurality of cells in fluid communication with the first plurality of apertures, each of the plurality of cells having cell walls defining a hollow space and at least one intercellular aperture being formed in each of the cell walls and extending from a first cell to a second cell; and
   a reduced-pressure source fluidly coupled to the contractible matrix and operable to deliver reduced pressure to the contractible matrix.

2. The reduced-pressure, tissue closure system of claim 1 wherein the contractible matrix is operable, when a reduced pressure is supplied by the reduced-pressure source, to develop a gripping force on a tissue adjacent to the first side of the contractible matrix and to move from an uncontracted position to a contracted position.

3. The reduced-pressure, tissue closure system of claim 1 wherein the contractible matrix is operable, when a reduced pressure is supplied by the reduced-pressure source, to develop a gripping force on a tissue adjacent to the first side of the contractible matrix and to generate the closing force on the tissue.

4. The reduced-pressure, tissue closure system of claim 1 wherein the contractible matrix comprises a honeycomb matrix.

5. The reduced-pressure, tissue closure system of claim 1 wherein the contractible matrix comprises a honeycomb matrix of thermoplastic elastomers.

6. The reduced-pressure, tissue closure system of claim 1 wherein the plurality of cells comprise a plurality of gear-shaped cells.

7. A contractible matrix adapted to be disposed proximate to tissue in a body cavity, the contractible matrix comprising:
   a first side and a second side,
   a plurality of apertures in the first side,
   cells in fluid communication with the plurality of apertures, each of the cells formed by an interconnected cell wall extending from the first side to the second side and defining a hollow space, and
   an intercellular aperture extending through each of the interconnected cell walls, wherein each intercellular aperture fluidly couples adjacent cells and extends from a first cell to a second cell.

8. The contractible matrix of claim 7, wherein the contractible matrix is formed from a material selected from the group consisting of: a thermal plastic elastomer and a thermoplastic urethane.

9. The contractible matrix of claim 7, wherein each of the cells is centered around one of the plurality of apertures.

10. The contractible matrix of claim 7, wherein the contractible matrix is operable to develop a gripping force on tissue adjacent to the first side and to move from an uncontracted position to a contracted position.

11. The contractible matrix of claim 7, wherein the contractible matrix comprises a honeycomb matrix of thermoplastic elastomers.

* * * * *